United States Patent [19]
Luengo

[11] Patent Number: 6,107,304
[45] Date of Patent: Aug. 22, 2000

[54] THIENO[2,3-B]PYRAZOLO[3,4-D]PYRIDINE-3-ONES TO ENHANCE ERYTHROPOIESIS

[75] Inventor: Juan Ignacio Luengo, Audubon, Pa.

[73] Assignee: SmithKline Beecham Corporation, Philadelphia, Pa.

[21] Appl. No.: 09/327,249

[22] Filed: Jun. 7, 1999

Related U.S. Application Data

[63] Continuation of application No. 09/101,128, filed as application No. PCT/US96/20418, Dec. 20, 1996, abandoned.
[60] Provisional application No. 60/009,371, Dec. 29, 1995, and provisional application No. 60/012,070, Feb. 22, 1996.

[51] Int. Cl.$^7$ ................... A61K 31/437; C07D 495/14; C07D 495/22
[52] U.S. Cl. ................ 514/278; 514/250; 514/257; 514/293; 514/287; 544/233; 544/245; 544/247; 544/343; 546/15; 546/41; 546/48; 546/64; 546/65; 546/83
[58] Field of Search ................ 546/15, 41, 48, 546/64, 65, 83; 544/233, 245, 247, 343; 514/278, 250, 257, 287, 293

[56] References Cited

FOREIGN PATENT DOCUMENTS 0 727 211 of 1996 European Pat. Off. .
0 728 482 of 1996 European Pat. Off. .

OTHER PUBLICATIONS

Kahn et al., J. Heterocyclic Chem., vol. 20, pp. 475–476 (Mar.–Apr. 1983).

Chemical Abstracts, vol. 89, No. 15, Abstract No. 129437q, p. 585 (Oct. 9, 1978).

*Primary Examiner*—Evelyn Mei Huang
*Attorney, Agent, or Firm*—James M. Kanagy; Charles M. Kinzig

[57] ABSTRACT

Invented are substituted thieno (2,3-b)pyrazolo(3,4-d) pyridin-3-ones, pharmaceutical compositions containing these compounds, and methods of using these compounds to enhance erythropoiesis. Also invented are intermediates and processess used in preparing these compounds.

7 Claims, No Drawings

THIENO[2,3-B]PYRAZOLO[3,4-D]PYRIDINE-3-ONES TO ENHANCE ERYTHROPOIESIS

This is a continuation of Ser. No. 09/101,128, abandoned which is a 371 of International Application PCT/U.S.96/20418, filed Dec. 20, 1996 which claims benefit from U.S. Provisional Applications 60/009,371, filed Dec. 29, 1995 and 60/012,070, filed Feb. 22, 1996.

BACKGROUND OF THE INVENTION typically, anemia of chronic renal failure results in reduced erythrocyte production due to diminished kidney erythropoietin (EPO) secretion. EPO is produced by the kidneys in response to renal delivery of oxygen and its principal site of action is the erythroid lineage in the bone marrow. It regulates the proliferation and differentiation of erythroid precursor cells allowing for adequate erythrocyte production. Clinical trials of replacement therapy in patients with end-stage renal disease have established that erythropoietin can correct anemia in these patients by enhancing erythropoiesis.

The ability to enhance erythropoiesis resulting from or independent of chronic renal failure is considered an attractive therapy for anemias, cytopenias, and other conditions with depressed erythrocyte production.

It would be desirable to provide compounds which allow for the enhancement of erythropoiesis.

As disclosed herein it has unexpectedly been discovered that certain selected thieno[2,3-b]pyrazolo[3,4-d]pyridin-3-ones are effective in enhancing erythropoiesis in mammals, including humans.

SUMMARY OF THE INVENTION

The present invention resides in the discovery that certain substituted thieno[2,3-b]pyrazolo[3,4-d]pyridin-3-ones enhance erythropoiesis in mammals, including humans.

Presently preferred compounds of the invention which are used in the invented pharmaceutical compositions and the invented methods include:

2,3,7,8,9,10-Hexahydro-4-methyl-1H-[1]benzothieno[2,3-b]pyrazolo[3,4-d]pyridin-3-one;

2,3-Dihydro-4-methyl-1H-[1]benzothieno[2,3-b]pyrazolo[3,4-d]pyridin-3-one;

8,8-Ethylenedioxy-2,3,7,8,9,10-hexahydro-4-methyl-1H-[1]benzothienol[2,3-b]pyrazolo[3,4-d]-pyridin-3-one;

1,4-Dimethyl-8,8-ethylenedioxy-2,3,7,8,9,10-hexahydro-1H-[1]benzothieno[2,3-b]pyrazolo[3,4-d]pyridin-3-one;

8-tert-Butoxycarbonyl-2,3,7,8,9,10-hexahydro-4-methyl-1H-pyrido[4',3':4,5]thieno[2,3-b]pyrazolo[3,4-d]pyridin-3-one; and 2,3,7,8,9,10-Hexahydro-4methyl-1H-pyrido[4',3':4,5]thieno[2,3-b]pyrazolo[3,4-d]pyridin-3one.

In a further aspect of the invention there are provided novel intermediates and novel processes useful in preparing the presently invented compounds.

Included in the present invention are pharmaceutical compositions comprising a pharmaceutical carrier and compounds useful in the methods of the invention.

DETAILED DESCRIPTION OF THE INVENTION

As used herein, the term "enhancing erythropoiesis" means increasing the production of erythrocytes.

As used herein, the term "treating" and derivatives thereof means prophylactic or therapeutic therapy.

The presently invented compounds of this invention that enhance erythropoiesis have the following Formula (I):

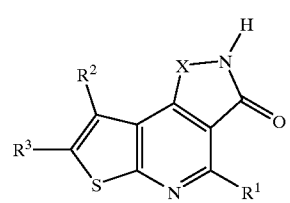

(I)

wherein:

X is O or $NR^5$, where $R^5$ is hydrogen, or selected from: linear or branched $C_{1-6}$alkyl, —$(CH_2)_nC_{3-7}$cycloalkyl, linear or branched $C_{2-6}$alkenyl, linear and branched $C_{2-6}$alkynyl or —$(CH_2)_n$Ar, all of which are optionally substituted with one or more substituents selected from the group consisting of: —OH, —$OR^6$, —$CONR^6R^7$, —$NR^6R^7$, —$COR^6$, —$CO_2R^6$, —$SO_2NHR^6$, —$NHCOR^6$ and halogen, wherein n is 0 to 6, and $R^6$ and $R^7$ are:

i) hydrogen, or independently selected from: H, linear or branched $C_{1-6}$alkyl, $C_{3-7}$cycloalkyl, linear or branched $C_{2-6}$alkenyl, linear or branched $C_{2-6}$alkynyl and Ar, all of which are optionally substituted with one or more substituents selected from the group consisting of: —OH and halogen, or (ii) when attached to the same nitrogen atom $R^6$ and $R^7$ can join together to form a ring selected from the group consisting of: piperidyl, morpholynyl, piperazinyl and pyrrolidyl;

$R^1$ is hydrogen, or selected from: linear or branched $C_{1-6}$alkyl, —$(CH_2)_nC_{3-7}$cycloalkyl, linear or branched $C_{2-6}$alkenyl, linear or branched $C_{2-6}$alkynyl and —$(CH_2)_n$Ar, all of which are optionally substituted with one or more substituents selected from the group consisting of:—OH, —$OR^6$, —$CONR^6R^7$, —$NR^6R^7$, —$COR^6$, —$CO_2R^6$, —$SO_2NHR^6$, —$NHCOR^6$ and halogen, where n, $R^6$ and $R^7$ have the same meaning as above;

and $R^2$ and $R^3$ are (i) hydrogen, or independently selected from: H, linear or branched $C_{1-6}$alkyl, —$(CH_2)_nC_{3-7}$cycloalkyl, linear or branched $C_{2-6}$alkenyl, linear or branched $C_{2-6}$alkynyl and —$(CH_2)_n$Ar, all of which are optionally substituted with one or more substituents selected from the group consisting of: —OH, —$OR^6$, —$CONR^6R^7$, —$NR^6R^7$, —$COR^6$, —$CO_2R^6$, —$SO_2NHR^6$, —$NHCOR^6$ and halogen, where n, $R^6$ and $R^7$ have the same meaning as above, (ii) $R^2$ and $R^3$ are joined together to form a non aromatic saturated or unsaturated $C_{3-12}$cycloalkyl, optionally containing one or two heteroatoms, and optionally substituted with one or more substituents selected from the group consisting of ethylenedioxy, linear or branched $C_{1-6}$alkyl, —$(CH_2)_nC_{3-7}$cycloalkyl, linear or branched $C_{2-6}$alkenyl, linear or branched $C_{2-6}$alkynyl, —$(CH_2)_nAr$, —OH, —$OR^6$, —$CONR^6R^7$, —$COR^6$, —$CO_2R^6$, —$SO_2NHR^6$, —$NHCOR^6$ and halogen,
where n, $R^6$ and $R^7$ have the same meaning as above, or (iii) $R^2$ and $R^3$ are joined together to form an aromatic ring selected from the group consisting of: phenyl, naphthyl, furyl, pyrrolyl, thienyl, isothiazolyl, imidazolyl, isoxazolyl, thiazolyl, oxazolyl, pyrazolyl, oxadiazolyl, triazolyl, tetrazolyl, pyridyl, pyrazinyl, pyrimidyl, pyridiazinyl, carbazolyl, indolyl, quinolyl and purinyl, all of which are optionally substituted with one or more substituents selected from the group consisting of halogen, —OH, linear or branched $C_{1-6}$alkyl, —$(CH_2)_nC_{3-7}$cycloalkyl, linear or branched $C_{2-6}$alkenyl, —$(CH_2)_nPh$, —O—$C_{1-6}$alkyl, —$CONR^6R^7$, —$NR^6R^7$, —$COR^6$, —$CO_2R^6$, —$SO_2NHR^6$, —$NHCOR^6$ and halogen,
where n, $R^6$ and $R^7$ have the same meaning as above;

or a pharmaceutically acceptable salt, hydrate or solvate thereof; except 2,3,7,8,9,10-Hexahydro-4-methyl-1H-[1]benzothieno[2,3-b]pyrazolo[3,4-d]pyridin-3-one and 8,8-Ethylenedioxy-2,3,7,8,9,10-hexahydro-4-methyl-1H-[1]benzothieno[2,3-b]pyrazolo[3,4-d]pyridin-3-one; but including pharmaceutically acceptable salts, hydrates and solvates of 2,3,7,8,9,10-Hexahydro-4-methyl-1H-[1]benzothieno[2,3-b]pyrazolo[3,4-d]pyridin-3-one and 8,8-Ethylenedioxy-2,3,7,8,9,10-hexahydro-4-methyl-1H-[1]benzothieno[2,3-b]pyrazolo[3,4-d]pyridin-3-one.

Preferred among the presently invented Formula (I) compounds are those having the following Formula (II):

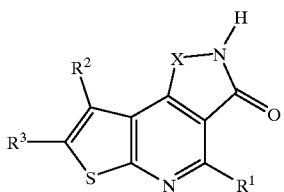

(II)

wherein:
X is O or $NR^5$,
where $R^5$ is hydrogen, or selected from: linear or branched $C_{1-6}$alkyl, —$(CH_2)_nC_{3-7}$cycloalkyl, linear or branched $C_{2-6}$alkenyl, linear and branched $C_{2-6}$alkynyl or —$(CH_2)_nAr$,
where n is 0 to 6;

$R^1$ is hydrogen, or selected from: linear or branched $C_{1-6}$alkyl, —$(CH_2)_nC_{3-7}$cycloalkyl, linear or branched $C_{2-6}$alkenyl, linear or branched $C_{2-6}$alkynyl and —$(CH_2)_nAr$,
where n has the same meaning as above; and $R^2$ and $R^3$ are
(i) hydrogen or independently selected from: linear or branched $C_{1-6}$alkyl, —$(CH_2)_nC_{3-7}$cycloalkyl, linear or branched $C_{2-6}$alkenyl, linear or branched $C_{2-6}$alkynyl and —$(CH_2)_nAr$,
where n has the same meaning as above, (ii) $R^2$ and $R^3$ are joined together to form a non aromatic saturated or unsaturated $C_{3-12}$cycloalkyl, optionally containing one nitrogen atom, and optionally substituted with one substituent selected from the group consisting of: ethylenedioxy, linear or branched $C_{1-6}$alkyl, —$(CH_2)_nC_{3-7}$cycloalkyl, liner or branched $C_{2-6}$alkenyl, linear or branched $C_{2-6}$alkynyl, —$(CH_2)_nAr$, —OH, —$OR^6$, —$CONR^6R^7$, —$COR^6$, —$CO_2R^6$, —$SO_2NHR^6$, —$NHCOR^6$ and halogen,
where n has the same meaning as above, or (iii) $R^2$ and $R^3$ are joined together to form an aromatic ring selected from the group consisting of: phenyl, naphthyl, furyl, pyrrolyl, thienyl, isothiazolyl, imidazolyl, isoxazolyl, thiazolyl, oxazolyl, pyrazolyl, oxadiazolyl, triazolyl, tetrazolyl, pyridyl, pyrazinyl, pyrimidyl, pyridazinyl, carbazolyl, indolyl, quinolyl and purinyl, all of which are optionally substituted with one or more substituents selected from the group consisting of: halogen, —OH, linear or branched $C_{1-6}$alkyl, —$(CH_2)_nC_{3-7}$cycloalkyl, linear or branched $C_{2-6}$alkenyl, —$(CH_2)_nPh$, —O—$C_{1-6}$alkyl and halogen,
where n has the same meaning as above;

or a pharmaceutically acceptable salt, hydrate or solvate thereof; except 2,3,7,8,9,10-Hexahydro-4-methyl-1H-[1]benzothieno[2,3-b]pyrazolo[3,4-d]pyridin-3-one and 8,8-Ethylenedioxy-2,3,7,8,9,10-hexahydro-4-methyl-1H-[1]benzothieno[2,3-b]pyrazolo[3,4-d]pyridin-3-one; but including pharmaceutically acceptable salts, hydrates and solvates of 2,3,7,8,9,10-Hexahydro-4-methyl-1H-[1]benzothieno[2,3-b]pyrazolo[3,4-d]pyridin-3-one and 8,8-Ethylenedioxy-2,3,7,8,9,10-hexahydro-4-methyl-1H-[1]benzothieno[2,3-b]pyrazolo[3,4-d]pyridin-3-one.

Preferred among the present invented Formula (II) compounds are those in which:
X is $NR^5$,
where $R^5$ is hydrogen, or selected from: linear or branched $C_{1-6}$alkyl, $C_{3-7}$cycloalkyl and phenyl;

$R^1$ is hydrogen, or selected from: linear or branched $C_{1-6}$alkyl, $C_{3-7}$cycloalkyl and phenyl; and $R^2$ and $R^3$ are
(i) hydrogen, or independently selected from: linear or branched $C_{1-6}$alkyl, $C_{3-7}$cycloalkyl and phenyl, (ii) $R^2$ and $R^3$ are joined together to form a non aromatic saturated or unsaturated $C_{5-7}$cycloalkyl, optionally containing one nitrogen heteroatom, and optionally substituted with one or more substituents selected from the group consisting of: ethylenedioxy, linear or branched $C_{1-6}$alkyl, $C_{3-7}$cycloalkyl, phenyl, —OH, —$OR^6$, —$CONR^6R^7$, —$COR^6$, —$CO_2R^6$, —$SO_2NHR^6$, —$NHCOR^6$ and halogen, or (iii) $R^2$ and $R^3$ are joined together to form a phenyl ring, optionally substituted with one or more substituents selected from the group consisting of: halogen, —OH, linear or branched $C_{1-6}$alkyl, $C_{3-7}$cycloalkyl and phenyl; except 2,3,7,8,9,10-Hexahydro-4-methyl-1H-[1]benzothieno[2,3-b]pyrazolo[3,4-d]pyridin-3-one and 8,8-Ethylenedioxy-2,3,7,8,9,10-hexahydro-4-methyl-1H-[1]benzothieno[2,3-b]pyrazolo[3,4-d]pyridin-3-one.

Preferred among the present invented compounds are:
2,3-Dihydro-4-methyl-1H-[1]benzothieno[2,3-b]pyrazolo[3,4-d]pyridin-3-one and pharmaceutically acceptable salts, hydrates and solvates thereof;

A pharmaceutically acceptable salt, hydrate or solvate of 2,3,7,8,9,10-Hexahydro-4-methyl-1H-[1]benzothieno[2,3-b]pyrazolo[3,4-d]pyridin-3-one;

1,4-Dimethyl-8,8-ethylenedioxy-2,3,7,8,9,10-hexahydro-1H-[1]benzothieno[2,3-b]pyrazolo[3,4-d]pyridin-3- one and pharmaceutically acceptable salts, hydrates and solvates thereof;

A pharmaceutically acceptable salt, hydrate or solvate of 8,8-Ethylenedioxy-2,3,7,8,9,10-hexahydro-4-methyl-1H-[1]benzothieno[2,3-b]pyrazolo[3,4-d]pyridin-3-one;

8-tert-Butoxycarbonyl-2,3,7,8,9,10-hexahydro-4-methyl-1H-pyrido[4',3':4,5]thieno[2,3-b]pyrazolo[3,4-d]pyridin-3-one and pharmaceutically acceptable salts, hydrates and solvates thereof; and 2,3,7,8,9,10-Hexahydro-4-methyl-1H-pyrido[4',3':4,5]thieno[2,3-b]pyrazolo[3,4-d]pyridin-3-one and pharmaceutically acceptable salts, hydrates and solvates thereof.

Compounds of the present invention that enhance erythropoiesis have the following Formula (III):

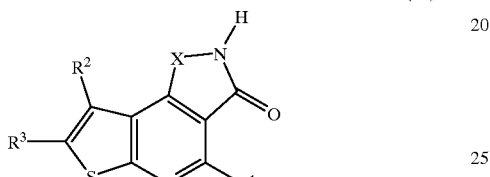

(III)

wherein:
X is O or $NR^5$,
where $R^5$ is hydrogen or selected from: linear or branched $C_{1-6}$alkyl, —$(CH_2)_nC_{3-7}$cycloalkyl, linear or branched $C_{2-6}$alkenyl, linear and branched $C_{2-6}$alkynyl or —$(CH_2)_n$Ar, all of which are optionally substituted with one or more substituents selected from the group consisting of: —OH, —$OR^6$, —$CONR^6R^7$, —$NR^6R^7$, —$COR^6$, —$CO_2R^6$, —$SO_2NHR^6$, —$NHCOR^6$ and halogen, where n is 0 to 6, and
$R^6$ and $R^7$ are:
(i) hydrogen, or independently selected from: H, linear or branched $C_{1-6}$alkyl, $C_{3-7}$cycloalkyl, linear or branched $C_{2-6}$alkenyl, linear or branched $C_{2-6}$alkynyl and Ar, all of which are optionally substituted with one or more substituents selected from the group consisting of: —OH and halogen; or
(ii) when attached to the same nitrogen atom $R^6$ and $R^7$ can join together to form a ring selected from the group consisting of: piperidyl, morpholynyl, piperazinyl and pyrrolidyl;

$R^1$ is hydrogen, or selected from: linear or branched $C_{1-6}$alkyl, —$(CH_2)_nC_{3-7}$cycloalkyl, linear or branched $C_{2-6}$alkenyl, linear or branched $C_{2-6}$alkynyl and —$(CH_2)_n$Ar, all of which are optionally substituted with one or more substituents selected from the group consisting of: —OH, —$OR^6$, —$CONR^6R^7$, —$NR^6R^7$, —$COR^6$, —$CO_2R^6$, —$SO_2NHR^6$, —$NHCOR^6$ and halogen,
where n, $R^6$ and $R^7$ have the same meaning as above; and $R^2$ and $R^3$ are
(i) hydrogen or independently selected from: H, linear or branched $C_{1-6}$alkyl, —$(CH_2)_nC_{3-7}$cycloalkyl, linear or branched $C_{2-6}$alkenyl, linear or branched $C_{2-6}$alkynyl and —$(CH_2)_n$Ar, all of which are optionally substituted with one or more substituents selected from the group consisting of: —OH, —$OR^6$, —$CONR^6R^7$, —$NR^6R^7$, —$COR^6$, —$CO_2R^6$, —$SO_2NHR^6$, —$NHCOR^6$ and halogen
where n, $R^6$ and $R^7$ have the same meaning as above, (ii) $R^2$ and $R^3$ are joined together to form a non aromatic saturated or unsaturated $C_{3-12}$cycloalkyl, optionally containing one or two heteroatoms, and optionally substituted with one or more substituents selected from the group consisting of: ethylenedioxy, linear or branched $C_{1-6}$alkyl, —$(CH_2)_nC_{3-7}$cycloalkyl, linear or branched $C_{2-6}$alkenyl, linear or branched $C_{2-6}$alkynyl, —$(CH_2)_n$Ar, —OH, —$OR^6$, —$CONR^6R^7$, —$COR^6$, —$CO_2R^6$, —$SO_2NHR^6$, —$NHCOR^6$ and halogen,
where n, $R^6$ and $R^7$ have the same meaning as above, or (iii) $R^2$ and $R^3$ are joined together to form an aromatic ring selected from the group consisting of: phenyl, naphthyl, furyl, pyrrolyl, thienyl, isothiazolyl, imidazolyl, isoxazolyl, thiazolyl, oxazolyl, pyrazolyl, oxadiazolyl, triazolyl, tetrazolyl, pyridyl, pyrazinyl, pyrimidyl, pyridazinyl, carbazolyl, indolyl, quinolyl and purinyl, all of which are optionally substituted with one or more substituents selected from the group consisting of: halogen, —OH, linear or branched $C_{1-6}$alkyl, —$(CH_2)_nC_{3-7}$cycloalkyl, linear or branched $C_{2-6}$alkenyl, —$(CH_2)_n$Ph, —O—$C_{1-6}$alkyl, —$CONR^6R^7$, —$NR^6R^7$, —$COR^6$, —$CO_2R^6$, —$SO_2NHR^6$, —$NHCOR^6$ and halogen,
where n, $R^6$ and $R^7$ have the same meaning as above;
or a pharmaceutically acceptable salt, hydrate or solvate thereof.

Preferred among above Formula (III) compounds of the present invention that enhance erythropoiesis are those having the following Formula (IV):

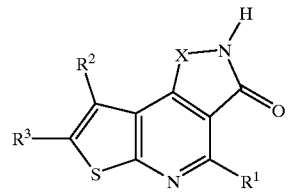

(IV)

wherein:
X is O or $NR^5$,
where $R^5$ is hydrogen, or selected from: linear or branched $C_{1-6}$alkyl, —$(CH_2)_nC_{3-7}$cycloalkyl, linear or branched $C_{2-6}$alkenyl, linear and branched $C_{2-6}$alkynyl or —$(CH_2)_n$Ar,
where n is 0 to 6;

$R^1$ is hydrogen, or selected from: linear or branched $C_{1-6}$alkyl, —$(CH_2)_nC_{3-7}$cycloalkyl, linear or branched $C_{2-6}$alkenyl, linear or branched $C_{2-6}$alkynyl and —$(CH_2)_n$Ar,
where n has the same meaning as above; and $R^2$ and $R^3$ are
(i) hydrogen, or independently selected from: linear or branched $C_{1-6}$alkyl, —$(CH_2)_nC_{3-7}$cycloalkyl, linear or branched $C_{2-6}$alkenyl, linear or branched $C_{2-6}$alkynyl and —$(CH_2)_n$Ar,
where n has the same meaning as above, (ii) $R^2$ and $R^3$ are joined together to form a non aromatic saturated or unsaturated $C_{3-12}$cycloalkyl, optionally containing one nitrogen atom, and optionally substituted with one substituent selected from the group consisting of: ethylenedioxy, linear or branched $C_{1-6}$alkyl, —$(CH_2)_nC_{3-7}$cycloalkyl, linear or branched $C_{2-6}$alkenyl, linear or branched $C_{2-6}$alkynyl, —$(CH_2)_nAr$, —OH, —$OR^6$, —$CONR^6R^7$, —$COR^6$, —$CO_2R^6$, —$SO_2NHR^6$, —$NHCOR^6$ and halogen, where n has the same meaning as above, or (iii) $R^2$ and $R^3$ are joined together to form an aromatic ring selected from the group consisting of: phenyl, naphthyl, furyl, pyrrolyl, thienyl, isothiazolyl, imidazolyl, isoxazolyl, thiazolyl, oxazolyl, pyrazolyl, oxadiazolyl, triazolyl, tetrazolyl, pyridyl, pyrazinyl, pyrimidyl, pyridazinyl, carbazolyl, indolyl, quinolyl and purinyl, all of which are optionally substituted with one or more substituents selected from the group consisting of: halogen, —OH, linear or branched $C_{1-6}$alkyl, —$(CH_2)_nC_{3-7}$cycloalkyl, linear or branched $C_{2-6}$alkenyl, —$(CH_2)_nPh$, —O—$C_{1-6}$alkyl and halogen, where n has the same meaning as above;

or a pharmaceutically acceptable salt, hydrate or solvate thereof.

Preferred among the presently invented Formula (IV) compounds are those in which:

X is $NR^5$,
where $R^5$ is hydrogen, or selected from: linear or branched $C_{1-6}$alkyl, $C_{3-7}$cycloalkyl and phenyl;

$R^1$ is hydrogen, or selected from: linear or branched $C_{1-6}$alkyl, $C_{3-7}$cycloalkyl and phenyl; and $R^2$ and $R^3$ are (i) hydrogen, or independently selected from: linear or branched $C_{1-6}$alkyl, $C_{3-7}$cycloalkyl and phenyl, (ii) $R^2$ and $R^3$ are joined together to form a non aromatic saturated or unsaturated $C_{5-7}$cycloalkyl, optionally containing one nitrogen heteroatom, and optionally substituted with one or more substituents selected from the group consisting of: ethylenedioxy, linear or branched $C_{1-6}$alkyl, $C_{3-7}$cycloalkyl, phenyl, —OH, —$OR^6$, —$CONR^6R^7$, —$COR^6$, —$CO_2R^6$, —$SO_2NHR^6$, —$NHCOR^6$ and halogen, or (iii) $R^2$ and $R^3$ are joined together to form a phenyl ring, optionally substituted with one or more substituents selected from the group consisting of: halogen, —OH, linear or branched $C_{1-6}$alkyl, $C_{3-7}$cycloalkyl and phenyl; except 2,3,7,8,9,10-Hexahydro-4-methyl-1H-[1]benzothieno[2,3-b]pyrazolo[3,4-d]pyridin-3-one and 8,8-Ethylenedioxy-2,3,7,8,9,10-hexahydro-4-methyl-1H-[1]benzothieno[2,3-b]pyrazolo[3,4-d]pyridin-3-one.

Preferred compounds of the present invention that enhance erythropoiesis are:

2,3,7,8,9,10-Hexahydro-4-methyl-1H-[1]benzothieno[2,3-b]pyrazolo[3,4-d]pyridin-3-one and pharmaceutically acceptable salts, hydrates and solvates thereof;

2,3-Dihydro-4-methyl-1H-[1]benzothieno[2,3-b]pyrazolo[3,4-d]pyridin-3-one and pharmaceutically acceptable salts, hydrates and solvates thereof;

8,8-Ethylenedioxy-2,3,7,8,9,10-hexahydro-4-methyl-1H-[1]benzothieno[2,3-b]pyrazolo[3,4-d]pyridin-3-one and pharmaceutically acceptable salts, hydrates and solvates thereof.

1,4-Dimethyl-8,8-ethylenedioxy-2,3,7,8,9,10-hexahydro-1H-[1]-benzothieno[2,3-b]pyrazolo[3,4-d]pyridin-3-one and pharmaceutically acceptable salts, hydrates and solvates thereof;

8-tert-Butoxycarbonyl-2,3,7,8,9,10-hexahydro-4-methyl-1H-pyrido[4',3':4,5]thieno[2,3-b]pyrazolo[3,4-d]pyridin-3-one and pharmaceutically acceptable salts, hydrates and solvates thereof; and 2,3,7,8,9,10-Hexahydro-4-methyl-1H-pyrido[4',3':4,5]thieno[2,3-b]pyrazolo[3,4-d]pyridin-3-one and pharmaceutically acceptable salts, hydrates and solvates thereof.

Compounds of Formula (III) are included in the pharmaceutical compositions of the invention and used in the methods of the invention.

By the term "AR" as used herein is meant phenyl, naphthyl, furyl, pyrrolyl, thienyl, isothiazolyl, imidazolyl, isoxazolyl, thiazolyl, oxazolyl, pyrazolyl, oxadiazolyl, triazolyl, tetrazolyl, pyridyl, pyrazinyl, pyrimidyl, pyridazinyl, carbazolyl, indolyl, quinolyl or purinyl.

By the term "$C_{x-y}$cycloalkyl" as used herein is meant a nonaromatic, unsaturated or saturated, cyclic or poly cyclic compound having from x to y carbons. When indicated, the term "$C_{x-y}$cycloalkyl" can include one or two heteroatoms.

Examples of $C_{x-y}$cycloalkyl as used herein include: cylcohexyl and cyclopentyl.

By the term "heteroatom" as used herein is meant O or N.

By the term "halogen" as used herein is meant F, Cl, Br or I.

Formula (I) compounds are prepared as shown in Scheme I below provided that the 'R' substituents do not include any such substituents that render inoperative the Scheme I process.

Scheme (I)

Preparation of Compounds of Formula (I)

Scheme (I) outlines the preparation of Fromula (I) compounds from Formula (2) compounds.

A ketone of Formula (2)

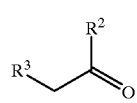

(2)

where $R^2$ and $R^3$ are as described above; is reacted with ethyl cyanoacetate, in a solvent, such as toluene, at reflux in the presence of of an amine, such as diethylamine, with azeotropic removal of water using a Dean-Stark apparatus to yield a cyano ester of Formula (3)

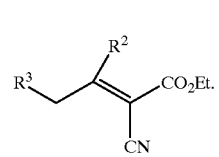

(3)

Reacting the cyano ester of Formula (3) with elemental sulfur in a solvent, preferably ethanol, in the presence of an amine, such as diethylamine, affords the thiophene-3-carboxylate of Formula (4)

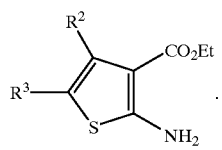
(4)

Compounds of Formula (4) are treated with a 3-ethoxycrotonate of Formula (5)

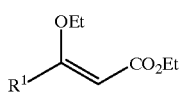
(5)

where $R_1$ is as described above; in a suitable solvent, such as toluene, at reflux in the presence of an acid catalyst, such as camphorsulfonic acid, and with azeotropic removal of water using a Dean-Stark trap. The resulting material is treated with 1 M sodium ethoxide solution and reflux to provide a thieno[2,3-b]pyridine of Formula (6)

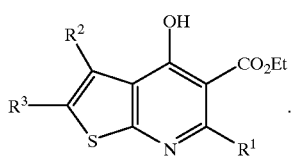
(6)

Treatment of the compound of Formula (6) with phosphorous oxychloride at reflux provideds the chlorothieno[2,3-b]pyridine of Formula (7)

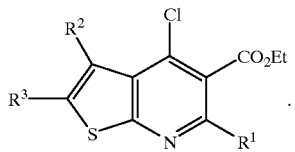
(7)

Treatment of the compound of Formula (6) with triflic anhydride in pyridine at 0° C. with aqueous work-up provides a triflate derivative of Formula (8)

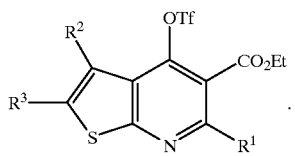
(8)

Reaction of either a compound of Formula (7) or compound of Formula (8) with a hydrazine derivative of Formula (9)

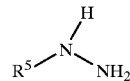
(9)

where $R^5$ is as described above; in a solvent, such as methanol, at reflux provides compounds of Formula (I), wherein X is $NR^5$.

Alternatively, treatment of either compound of Formula (7) or compound of Formula (8) with the hydroxylamine of Structure (10)

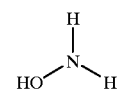
(10)

in a solvent, such as methanol, at reflux and in the presence of a base, such as triethylamine or sodium hydroxide, provides compounds of Formula (I), wherein X is O.

Pharmaceutically acceptable salts, hydrates and solvates of the compounds with the scope of this invention are formed when appropriate by methods well known to those of skill in the art.

In preparing the presently invented compounds of Formula (I), novel intermediates of the following Formula (V) are synthesized:

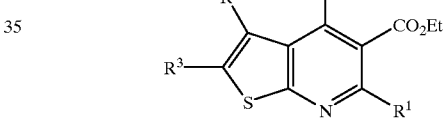
(V)

in which $R^1$ is as described in Formula (I); and $R^2$ and $R^3$ are joined together to form a non aromatic saturated or unsaturated $C_{3-12}$cycloalkyl, optionally containing one or two heteroatoms, and optionally substituted with one or more substituents selected from the group consisting of: ethylenedioxy, linear or branched $C_{1-6}$alkyl, —$(CH_2)_nC_{3-7}$cycloalkyl, linear or branched $C_{2-6}$alkenyl, linear or branched $C_{2-6}$alkynyl, —$(CH_2)_n$Ar, —OH, —$OR^6$, —$CONR^6R^7$, —$COR^6$, —$CO_2R^6$, —$SO_2NHR^6$, —$NHCOR^6$ and halogen, where n, $R^6$ and $R^7$ have the same meaning as in Formula (I).

A preferred process for preparing a compound of Formula (I)

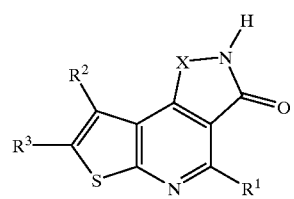
(I)

in which X is $NR^5$ and $NR^5$, $R^1$, $R^2$ and $R^3$ are as described in Formula (I) above, including the exceptions, and pharmaceutically acceptable salts, hydrates and solvates thereof comprises reacting a compound of the formula $$\text{[structure: R}^2\text{, R}^3\text{, Cl, CO}_2\text{Et, S, N, R}^1\text{ thienopyridine]}$$

in which $R^1$, $R^2$ and $R^3$ are as described above with a hydrazine derivative of the formula $$R^5-\overset{H}{N}-NH_2$$

where $R^5$ is as described in Formula (I) above;

in a solvent, such as methanol, at reflux and thereafter optionally forming a pharmaceutically acceptable salt, hydrate or solvate thereof.

A preferred process for preparing a compound of Formula (I)

$$\text{[structure (I): X—N(H), R}^2\text{, R}^3\text{, S, N, R}^1\text{, =O]}$$

in which X is $NR^5$ and $NR^5$, $R^1$, $R^2$ and $R^3$ are as described in Formula (I) above, including the exceptions, and pharmaceutically acceptable salts, hydrates and solvates thereof comprises reacting a compound of the Formula $$\text{[structure: R}^2\text{, R}^3\text{, OTf, CO}_2\text{Et, S, N, R}^1\text{]}$$

in which $R^1$, $R^2$ and $R^3$ are as described above with a hydrazine derivative of the formula $$R^5-\overset{H}{N}-NH_2$$

where $R^5$ is as described in Formula (I) above;

in a solvent, such as methanol, at reflux and thereafter optionally forming a pharmaceutically acceptable salt, hydrate or solvate thereof.

A preferred process for preparing a compound of Formula (I)

$$\text{[structure (I)]}$$

in which X is O and $R^1$, $R^2$ and $R^3$ are as described in Formula (I) above, including the exceptions, and pharmaceutically acceptable salts, hydrates and solvates thereof comprises reacting a compound of the Formula $$\text{[structure: R}^2\text{, R}^3\text{, Cl, CO}_2\text{Et, S, N, R}^1\text{]}$$

in which $R^1$, $R^2$ and $R^3$ are as described above with the hydroxylamine of the Structure $$HO-\overset{H}{N}-H$$

in a solvent, such as methanol, at reflux and in the presence of a base, such as triethylamine or sodium hydroxide, and thereafter optionally forming a pharmaceutically acceptable salt, hydrate or solvate thereof.

A preferred process for preparing a compound of Formula (I)

$$\text{[structure (I)]}$$

in which X is O and $R^1$, $R^2$ and $R^3$ are as described in Formula (I) above, including the exceptions, and pharmaceutically acceptable salts, hydrates and solvates thereof comprises reacting a compound of the Formula $$\text{[structure: R}^2\text{, R}^3\text{, OTf, CO}_2\text{Et, S, N, R}^1\text{]}$$

in which $R^1$, $R^2$ and $R^3$ are as described above with the hydroxylamine of the Structure

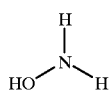

in a solvent, such as methanol, at reflux and in the presence of a base, such as triethylamine or sodium hydroxide, and thereafter optionally forming a pharmaceutically acceptable salt, hydrate or solvate thereof.

Because the pharmaceutically active compounds of the present invention enhance erythropoiesis they have therapeutic utility in treating anemias, cytopenias and other conditions with depressed erythrocyte production.

In determining the potency of the compounds of this invention to enhance erythropoiesis the following procedure was employed.

Effect of Compounds of the Present Invention on the Cell Growth of the Erythropoietin (EPO) Dependent UT7/EPO Human Cell Line Ut7/EPO cells express human EPO receptors on their cell surface and respond to EPO by cell proliferation. Proliferation of UT7/EPO cells in response to EPO or to compounds of the present invention was quantitated using a MTT assay as described in T. Mosmann (1983) *J. Immunol. Methods* Rapid colorimetric assay for cellular growth and survival: Application to proliferation and cytotoxicity assays 65:55–63. UT7/EPO cells were grown in growth medium (Iscove's Modified Dulbecco's Medium with L-glutamine and 25 mM HEPES buffer) (IMDM medium) with 0.4 U/ml recombinant human EPO (Amgen) and 10% fetal bovine serum (FBS) to a cell density of approximately $5\times10^5$ cells/ml. Cells were collected by centrifugation (~600×g) and washed twice in IMDM without EPO or FBS. The cells were resuspended at $5\times10^5$ cells/ml in IMDM medium with 10% FBS or serum-free medium. One hundred microliter aliquots were added to wells in a 96 well microtiter plate. A compound of the present invention (or EPO) was added to the wells by serial dilution, maintaining a final volume of 0.1 ml. The treated cells were incubated in a humidified incubator at 37° C. and 5% $CO_2$ for 2–3 days. At the end of the incubation period, 0.04 mg MTT [3-[4,5-Dimthylthiazol-2-y]-2,5-diphenyltetrazolium bromide] was added to every well in a volume of 0.025 ml and incubated for 4 hours. The MTT reaction was stopped by addition of 10% SDS in 0.01N HCL and solubilized overnight at 37° C. Proliferation was quantitated colorimetrically at 570/750 nM using a BioTek II Microplate Reader. The increase in $OD_{570/750}$ is proportional to cell growth.

Compounds within the scope of this invention have been tested and have shown an $EC_{50}$ activity from 1 (uM) to >66 (uM) of MTT activity in UT7/EPO cells. Particularly preferred among the compounds of the invention and the compounds used in the invented pharmaceutical compositions and invented methods are:

2,3-Dihydro-4methyl-1H-[1]benzothieno[2,3-b]pyrazolo[3,4-d]pyridin-3-one and pharmaceutically acceptable salts, hydrates and solvates thereof;

A pharmaceutically acceptable salt, hydrate or solvate of 2,3,7,8,9,10-Hexahydro-4-methyl-1H-[1]benzothieno[2,3-b]pyrazolo[3,4-d]pyridin-3-one;

1,4-Dimethyl-8,8-ethylenedioxy-2,3,7,8,9,10-hexahydro-1H-[1]benzothieno[2,3-b]pyrazolo[3,4-d]pyridin-3-one and pharmaceutically acceptable salts, hydrates and solvates thereof;

A pharmaceutically acceptable salt, hydrate or solvate of 8,8-Ethylenedioxy-2,3,7,8,9,10-hexahydro-4-methyl-1H-[1]benzothieno[2,3-b]pyrazolo[3,4-d]pyridin-3-one;

8-tert-Butoxycarbonyl-2,3,7,8,9,10-hexahydro-4-methyl-1H-pyrido[4',3':4,5]thieno[2,3-b]pyrazolo[3,4-d]pyridin-3-one and pharmaceutically acceptable salts, hydrates and solvates thereof; and 2,3,7,8,9,10-Hexahydro-4-methyl-1H-pyrido[4',3':4,5]thieno[2,3-b]pyrazolo[3,4-d]pyridin-3-one and pharmaceutically acceptable salts, hydrates and solvates thereof.

Compounds within the scope of this invention have also stimulated proliferation of UT7/EPO cells in the presence of a suboptimal concentration of EPO.

The pharmaceutically active compounds within the scope of this invention are useful in enhancing erythropoiesis in mammals, including humans, in need thereof.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001 mg per kg and 100.0 mg per kg of subject body weight, preferably 0.001–10 mg/kg. The active compounds may be administered to a patient in need of enhanced erythropoiesis by any conventional route of administration, including, but not limited to, intravenous, intramuscular, oral, subcutaneous, intradermal, and parenteral. When treating a human patient in need of enhanced erythropoiesis, the selected dose is administered preferably from 1–6 times daily, orally or parenterally. Preferred forms of parenteral administration include topically, rectally, transdermally, by injection and continuously by infusion. Oral dosage units for human administration preferably contain from 0.005 to 500 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular pharmaceutically active compound in use, the strength of the preparation, the mode of administration, and the advancement of the disease condition. Additional factors depending on the particular patient being treated will result in a need to adjust dosages, including patient age, weight, diet, and time of administration.

The method of this invention of enhancing erythropoiesis in mammals, including humans, comprises administering to a subject in need of such therapy an effective erythropoiesis enhancing amount of a pharmaceutically active compound of the present invention.

The invention also provides for the use of a compound of Formula (III) in the manufacture of a medicament for use in enhancing erythropoiesis.

The invention also provides for a pharmaceutical composition for use in the treatment of anemias which comprises a compound of Formula III and a pharmaceutically acceptable carrier.

The invention also provides for a pharmaceutical composition for use in the treatment of cytopenias which comprises a compound of Formula III and a pharmaceutically acceptable carrier.

The invention also provides for a process for preparing a pharmaceutical composition containing a pharmaceutically acceptable carrier or diluent and a compound of Formula III which comprises bringing the compound of Formula III into association with the pharmaceutically acceptable carrier or diluent.

No unacceptable toxicological effects are expected when compounds of the invention are administered in accordance with the present invention.

In addition, the pharmaceutically active compounds of the present invention can be co-administered with further active ingredients, such as other compounds known to enhance erythropoiesis.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXPERIMENTAL DETAILS

EXAMPLE 1

Preparation of 2,3,7,8,9,10-Hexahydro-4-methyl-1H-[1]benzothieno[2,3-b]pyrazolo[3,4-d]pyridin-3-one

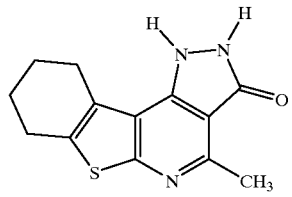

a) Ethyl 4-Hydroxy-2-methyl-5,6,7,8-tetrahydro-[1]benzothieno[2,3-b]pyridine-2-carboxylate A solution of ethyl 2-amino-4,5,6,7-tetrahydrobenzo[b]thiophene-3-carboxylate (8.9 g, 39 mmol) and ethyl 3-ethoxycrotonate (12.4 g, 78 mmol) in toluene (300 mL) was treated with camphorsulfonic acid (0.78 g, 3.4 mmol) and the reaction mixture was heated at reflux for 3 h using a Dean Stark trap. The mixture was then cooled to room temperature and was subsequently treated with a freshly prepared 1 M solution of sodium ethoxide (48 mL, 48 mmol). After addition was complete the reaction mixture was heated at reflux for 3 h. The mixture was cooled, concentrated and the residue dissolved in ethyl acetate. Acetic acid (2 mL) was added, solvent evaporated and resulting solid triturated with methanol to yield the title compound as an off-white solid (8.4 g, 74%); mp 140° C.; $^1$H NMR (400 MHz, CDCl$_3$) δ4.48 (q, J=7.2 Hz, 2 H), 3.04 (br s, 2 H), 2.81 (s, 3 H), 2.80 (br s, 2 H), 1.87 (br s, 4 H), 1.47 (t, J=7.2 Hz, 3 H); Anal. Calcd. for C$_{15}$H$_{17}$NO$_3$S: C, 61.83; H, 5.88; N, 4.81; Found: C, 61.69; H, 5.81; N, 4.73.

b) Ethyl 4-Chloro-2-methyl-5,6,7,8-tetrahydro-[1]benzothieno[2,3-b]pyridine-2-carboxylate A solution of compound of Example 1(a) (8.0 g, 27.4 mmol) in phosphorus oxychloride (100 mL) was refluxed for 3.5 hours. The phosphorus oxychloride was removed under vacuum and the residual oil was dissolved in ethyl acetate, washed with 5% aqueous sodium bicarbonate and dried over anhydrous sodium sulfate. Evaporation of the solvent provided the title compound as a crystalline solid (8.5 g, 95%). mp 65–66° C.; $^1$H NMR (400 MHz, CDCl$_3$) δ4.47 (q, J=7.1 Hz, 2 H), 3.10 (br s, 2 H), 2.85 (br s, 2 H), 2.60 (s, 3 H), 1.89 (br s, 4 H), 1.43 (t, J=7.1 Hz, 3 H); Anal. Calcd. for C$_{15}$H$_{16}$ClNO$_2$S.⅝H$_2$O: C, 57.73; N, 4.49; Found: C, 57.69; H, 5.08; N, 4.30.

c) 2,3,7,8,9,10-Hexahydro-4-methyl-1H-[1]benzothieno[2,3-b]pyrazolo[3,4-d]pyridin-3-one Hydrochloride Salt A solution of compound of Example 1(b) (2.0 g, 6.4 mmol) in methanol (50 mL) was treated with hydrazine monohydrate (10 mL) and the resulting mixture was heated at reflux for 16 h. The reaction was poured over diluted aqueous hydrochloric acid and the title compound precipitated as a yellow solid (1.8 g). $^1$H NMR (400 MHz, d$_4$-MeOH) δ3.01 (br s, 2 H), 3.00 (s, 3 H), 2.92 (br s, 2 H), 2.00 (br s, 4 H); Anal. Calcd. for C$_{13}$H$_{13}$N$_3$OS.HCl.¼H$_2$O: C, 52.00; H, 4.87; N, 13.99; Found: C, 51.92; H, 5.01; N, 13.70.

EXAMPLE 2

Preparation of 2,3-Dihydro-4-methyl-1H-[1]benzothieno[2,3-b]pyrazolo[3,4-d]pyridin-3-one

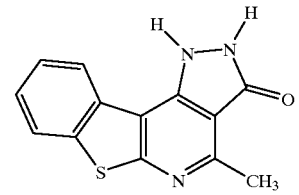

a) Ethyl 4-Chloro-2-methyl-[1]benzothieno[2,3-b]pyridine-2-carboxylate

A solution of compound of Example 1(b) (400 mg, 1.3 mmol) in toluene (20 mL) was treated with DDQ (1.8 g, 8.0 mmol) and the resulting suspension was refluxed at 100° C. for 24 h. The mixture was filtered off, the solvent evaporated and the crude material was purified by flash chromatography (silica gel, 9:1 hexane:ethyl acetate) to provide a the title compound as a solid material (400 mg): mp 111–112° C.; Anal. Calcd. for C$_{15}$H$_{12}$ClNO$_2$S; C, 58.92; H, 3.96; N, 4.58; Found: C, 58.78; H, 3.84; N, 4.56.

b) 2,3-Dihydro-4-methyl-1H-[1]benzothieno[2,3-b]pyrazolo[3,4-d]pyridin-3-one

A solution of compound of Example 2(a) (160 mg, 0.52 mmol) in methanol (10 mL) was treated with hydrazine monohydrate (2 mL) and the resulting mixture was heated at reflux for 24 h. After concentrating the solution under reduced pressure it was poured over diluted aqueous hydrochloric acid; the title compound precipitated as a yellow solid (140 mg, 90%): Anal. Calcd. for C$_{13}$H$_9$N$_3$OS.0.25H$_2$O: C, 59.01; H, 3.81; N, 15.90; Found: C, 59.38; H, 3.80; N, 15.58.

EXAMPLE 3

Preparation of 8,8-Ethylenedioxy-2,3,7,8,9,10-hexahydro-4-methyl-1H-[1]benzothieno[2,3-b]pyrazolo[3,4-d]pyridin-3-one

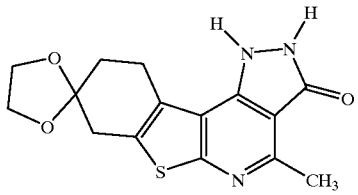

a) Ethyl 2-Cyano-2-(4,4,-ethylenedioxycyclohexylidene) acetate

To a mixture of 1,4 cyclohexanedione monoethylene ketal (25 g, 0.160 mol) and ethyl cyanoacetate (18 g, 0.160 mol) in toluene (400 mL) was added dropwise diethylamine (25 g, 0.337 mol) at room temperature. The reaction mixture was heated at reflux overnight (using a Dean Stark apparatus). The mixture was cooled and partitioned with ethyl acetate and saturated aqueous sodium bicarbonate (3×). The organic extracts were dried over sodium sulfate, filtered, concentrated in vacuo and recrystallized from ethanol to yield the title compound as an white solid (15.8 g, 45%). mp 80–81° C.; $^1$H NMR (400 MHz, CDCl$_3$) δ4.28 (q, J=7.2 Hz, 2 H), 4.00 (s, 4 H), 3.18 (t, J=6.5 Hz, 2 H), 2.85 (t, J=6.5 Hz, 2 H), 1.89 (t, J=6.5 Hz, 2 H), 1.82 (t, J=6.5 Hz, 2 H), 1.35 (t, J=7.1 Hz, 3 H).

b) Ethyl 2-Amino-6,6-ethylenedioxy-4,5,6,7-tetrahydrobenzo[b]thiophene-3-carboxylate To a suspension of compound of Example 3(a) (10 g, 45.6 mmol), sulfur (1.6 g, 50.2 mmol) in ethanol (164 mL) at 0° C., was added dropwise a solution of diethylamine (3.6 g, 50.2 mmol) in ethanol (26 mL). The resulting solution stirred at 0° C. for 1 h, then at room temperature for 3.5 h. The reaction mixture was quenched with ethyl acetate and partitioned with saturated aqueous ammonium chloride solution. The aqueous phase was extracted with ethyl acetate, and the organic extracts were washed with brine. The combined organic extracts were dried over sodium sulfate, filtered, concentrated in vacuo and chromatographed (silica gel, gradient 5 to 10% CH$_2$Cl$_2$:EtOAc) to yield the title compound as an oil (11.3 g, 87%). $^1$H NMR (400 MHz, CDCl$_3$) δ4.25 (q, J=7.1 Hz, 2 H), 4.02 (s, 4 H), 2.92 (t, J=6.5 Hz, 2 H), 2.74 (s, 2 H), 1.90 (t, J=6.6 Hz, 2 H), 1.33 (t, J=7.1, 3 H).

c) Ethyl 7,7-Ethylenedioxy-4-hydroxy-2-methyl-5,6,7,8-tetrahydro-[1]benzothieno[2,3-b]pyridine-2-carboxylate To a solution of compound of Example 3(b) (11.2 g, 39.5 mmol) in toluene (307 mL) at room temperature was added ethyl 3-ethoxycrotonate (12.4 g, 78.6 mmol) and camphorsulfonic acid (0.78 g, 3.4 mmol). The reaction mixture was heated at reflux for 3.5 h using a Dean Stark trap. The mixture was then cooled, and to it was added dropwise a freshly prepared solution of 1 M sodium ethoxide (49 mL). Once the addition was complete the reaction mixture was heated at reflux for 3 h. The mixture was cooled and the precipitate was filtered. After dissolving the salt in methanol (60 mL), it was added water (500 mL) and acetic acid (2 mL) to yield the title compound as a yellow solid (10.4 g, 76%). mp 94–95° C.; $^1$H NMR (400 MHz, CDCl$_3$) δ4.48 (q, J=7.1 Hz, 2 H), 4.06 (s, 4 H), 3.26 (t, J=6.5 Hz, 2 H), 3.02 (s, 2 H), 2.81 (s, 3 H), 2.02 (t, J=6.5, 2 H), 1.47 (t, J=7.1 Hz, 3 H); MS (ESI) m/z 350 [M+H]$^+$; Anal. Calcd. for C$_{17}$H$_{19}$NO$_5$S; C, 58.44; H, 5.48; N, 4.01; Found: C, 58.34; H, 5.46; N, 3.86.

d) Ethyl 7,7-Ethylenedioxy-4-trifluoromethylsulfonyloxy-2-methyl-5,6,7,8-tetrahydro-[1]benzothieno[2,3-b]pyridine-3-carboxylate To a solution of compound of Example 3(c) (5.0 g, 14.3 mmol) in pyridine (50 mL) was added dropwise triflic anhydride (4.0 g, 14.2 mmol). The reaction mixture was then stirred at 0° C. for 4 h until complete. The reaction mixture was washed with aqueous copper sulfate solution (3×) followed by water (2×), and brine (2×). The organic layer evaporated, dried over anhydrous sodium sulfate and concentrated in vacuo. Purification by flash chromatography (silica gel, 1:1 hexane:ethyl acetate) yielded the title compound as a light yellow solid (3.7 g, 54%). mp 133–134° C.; $^1$H NMR (400 MHz, CDCl$_3$) δ4.43 (q, J=7.2 Hz, 2 H), 4.06 (s, 4. H), 3.16 (t, J=6.5 Hz, 2 H), 3.10 (s, 2 H), 2.77 (s, 3 H), 2.03 (t, J=6.8 Hz, 2 H), 1.41 (t, J=7.1 Hz, 3 H); MS (ESI) m/z 482 [M+H]$^+$; Anal. Calcd. for C$_{18}$H$_{18}$F$_3$NO$_7$S$_2$; C, 44.90; H, 3.77; N, 2.91; Found: C, 45.03; H, 3.62; N, 2.89.

e) 8,8-Ethylenedioxy-2,3,7,8,9,10-hexahydro-4-methyl-1H-[1]benzothieno[2,3-b]pyrazolo[3,4-d]pyridin-3-one To a solution of compound of Example 3(d) (2.4 g, 5.0 mmol) in methanol (40 mL) at room temperature was added hydrazine monohydrate (4.1 g, 82.3 mmol). The reaction mixture was heated at reflux for 3 h. The mixture was cooled then partitioned between pH 7 aqueous buffer and ethyl acetate. The organic layer was dried over anhydrous sodium sulfate, filtered, concentrated in vacuo and recrystallized from methanol/ethyl acetate to yield the title compound as a light yellow solid (0.99 g, 60%). $^1$H NMR (400 MHz, d$_4$-MeOH) δ4.05 (s, 4 H), 3.15 (t, J=6.5 Hz, 2 H), 3.04 (s, 2 H), 2.82 (s, 3 H), 2.06 (t, J=6.5 Hz, 2 H); MS (ESI) m/z 318 [M+H]$^+$; Anal. Calcd. for C$_{15}$H$_{15}$N$_3$O$_3$S.0.25 H$_2$O: C, 55.97; H, 4.85; N, 13.05; Found: C, 55.85; H, 4.75; N, 13.30.

EXAMPLE 4

Preparation of 1,4-Dimethyl-8,8-ethylenedioxy-2,3,7,8,9,10-hexahydro-1H-[1]benzothieno[2,3-b]pyrazolo[3,4-d]pyridin-3-one

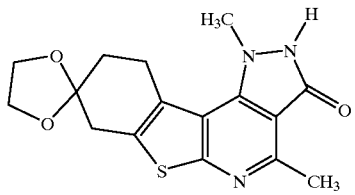

1,4-Dimethyl-8,8-ethylenedioxy-2,3,7,8,9,10-hexahydro-1H-[1]benzothieno[2,3-b]pyrazolo[3,4-d]pyridin-3-one A solution of compound of Example 3(d) (0.4 g, 0.83 mmol) in methanol (6.7 mL) at room temperature was treated with methylhydrazine (0.16 g, 3.45 mmol) and the mixture is heated at reflux for 2 h. The mixture was cooled and the precipitate, containing 150 mg of the 2,4-dimethyl regioisomer, filtered. The filtrate was evaporated and purified by flash cromatography (silica gel, elution with 80:20:5 ethyl acetate:methanol:acetic acid) to provide the title compound as a yellow solid (22 mg). $^1$H NMR (400 MHz, CDCl$_3$) δ4.03 (s, 4 H), 3.73 (s, 3 H), 3.76 (t, J=6.0 Hz, 2 H), 3.00 (s, 2 H), 2.80 (s, 3 H), 2.03 (t, J=6.0 Hz, 2 H); MS (ESI) m/z 332 (M+H)$^+$.

EXAMPLE 5

Preparation of 8-tert-Butoxycarbonyl-2,3,7,8,9,10-hexahydro-4-methyl-1H-pyrido[4',3':4,5]thieno[2,3-b]pyrazolo[3,4-d]pyridin-3-one

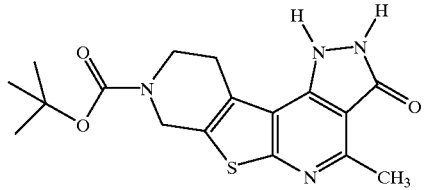

a) N-tert-Butoxycarbonyl-4-(1-cyano-1-ethoxycarbonyl)methylenepiperidine

To a mixture of N-tert-butoxycarbonyl-4-piperidone (25 g, 0.125 mol) and ethyl cyanoacetate (18 g, 0.160 mol) in toluene (400 mL) was added dropwise diethylamine (18.25 g, 0.25 mol) at room temperature. The reaction mixture was heated at reflux overnight, using a Dean Stark apparatus. The mixture was cooled and partitioned with ethyl acetate and saturated aqueous sodium bicarbonate (3x). The organic extracts were dried over sodium sulfate, filtered, concentrated in vacuo to yield 38 g of crude material. Purification by silica gel chromatography (70:30 hexanes:ethyl acetate) afforded the title compound as a white solid (22.2 g, 60%). $^1$H NMR (300 MHz, CDCl$_3$) δ4.31 (q, J=7.1 Hz, 2 H), 3.63 (t, J=5.5 Hz, 2 H), 3.56 (t, J=5.5 Hz, 2 H), 3.12 (t, J=5.5 Hz, 2 H), 2.78 (t, J=5.5 Hz, 2 H), 2.83 (s, 3 H), 1.48 (s, 9 H), 1.35 (t, J=7.1 Hz, 3 H); MS (ESI) m/a 295 [M+H]$^+$.

b) Ethyl 2-Amino-8-tert-butoxycarbonyl-4,5,6,7-tetrahydropyrido[4',3':4,5]thiophene-3-carboxylate To a suspension of compound of Example 5(a) (17 g, 58 mmol) and sulfur (2.08 g, 65 mmol) in ethanol (160 mL) at 0° C., was added dropwise a solution of diethylamine (4.75 g, 65 mmol) in ethanol (160 mL) and the mixture was stirred at 0° C. for 1 h, then at room temperature for 15 h. The resulting solid precipitate was filtered and the filtrate was diluted with water to afford an additional amount of precipitate. Overall, 15.6 g of title compound was obtained (82.5%): mp 153–154° C.; $^1$H NMR (400 MHz, CDCl$_3$) δ4.35 (s, 2 H), 4.27 (q, J=7.2 Hz, 2 H), 3.62 (t, J=5.8 Hz, 2 H), 2.80 (t, J=5.8 Hz, 2 H), 1.48 (s, 9 H), 1.34 (t, J=7.2 Hz, 3 H).

c) Ethyl 7-tert-Butoxycarbonyl-4-hydroxy-2-methyl-5,6,7,8-tetrahydropyrido[4',3':4,5]thieno[2,3-b]pyridine-2-carboxylate A solution of compound of Example 5(b) (14.0 g, 42.9 mmol) in toluene (300 mL) at room temperature was treated with ethyl 3-ethoxycrotonate (13.6 g, 85.8 mmol) and camphorsulfonic acid (1.0 g, 4.3 mmol) and the resulting mixture was heated at reflux for 3.5 h using a Dean Stark trap. After cooling, the reaction mixture was treated with a solution of sodium ethoxide (55 mmol) in ethanol (60 mL). Once the addition was complete the reaction mixture was heated at reflux for 3 h. The mixture was cooled and neutralized with acetic acid to pH 6. It was then extracted with ethyl acetate and the resulting solution was dried over sodium sulfate, filtered, concentrated in vacuo to yield 14.5 g of an oily material. Purification by silica gel chromatography (95:5 dichloromethane:ethyl acetate) afforded the title compound as a white solid (11.5 g, 77%); $^1$H NMR (300 MHz, CDCl$_3$) δ12.8 (s, 1 H), 4.65 (s, 2 H), 4.49 (q, J=7.1 Hz, 2 H), 3.75 (t, J=5.6 Hz, 2 H), 3.13 (t, J=5.6 Hz, 2 H), 2.83 (s, 3 H), 1.50 (s, 9 H), 1.48 (t, J=7.1 Hz, 3 H).

d) Ethyl 7-tert-Butoxycarbonyl-2-methyl-4-trifluoromethylsulfonyloxy-5,6,7,8-tetrahydropyrido[4'3':4,5]thieno[2,3-b]pyridine-2-carboxylate To a solution of compound of Example 5(c) (3.48 g, 10 mmol) in pyridine (25 mL) was added dropwise triflic anhydride (6.0 g, 2.5 mmol) under argon at −30° C. The reaction mixture was then stirred at −30° C. for 30 min and at room temperature for 1 h. It was subsequently washed with aqueous copper sulfate solution (3x) followed by water (2x), and brine (2x). The organic layer was evaporated, dried over anhydrous sodium sulfate and concentrated in vacuo to afford the title compound as a light yellow solid (4.38 g, 83.5%). $^1$H NMR (400 MHz, CDCl$_3$) δ4.73 (s, 2 H), 4.44 (q, J=7.1 Hz, 2 H), 3.75 (t, J=5.6 Hz, 2 H), 3.05 (t, J=5.6 Hz, 2 H), 2.79 (s, 3 H), 1.51 (s, 9 H), 1.42 (t, J=7.1 Hz, 3 H); MS (ESI) m/z 525 [M+H]$^+$.

e) 8-tert-Butoxycarbonyl-2,3,7,8,9,10-hexahydro-4-methyl-1H-pyrido[4',3':4,5]thieno[2,3-b]pyrazolo[3,4-d]pyridin-3-one To a solution of compound of Example 5(d) (4.0 g, 7.6 mmol) in methanol (50 mL) at room temperature was added hydrazine monohydrate (3.0 g, 75 mmol). The reaction mixture was heated at reflux for 15 h. The mixture was concentrated to about 10 mL of solvent and it was then diluted with water. The resulting solid material was filtered to provide the title compound as a white powder (1.7 g, 62%). mp>300° C. $^1$H NMR (400 MHz, d$_6$-DMSO) δ4.63 (s, 2 H, 3.71 (t, J=5.6 Hz, 2 H), 3.33 (t, J=5.6 Hz, 2 H), 2.69 (s, 3 H), 1.44 (s, 9 H); Anal. Calcd. for C$_{17}$H$_{20}$N$_4$O$_3$S: C, 56.65; H, 5.59; N, 15.54; Found: C, 56.59; H, 5.63; N, 15.55; MS (ESI) m/z 361 [M+H]$^+$.

EXAMPLE 6

Preparation of 2,3,7,8,9,10-Hexahydro-4-methyl-1H-pyrido[4',4':4,5]thieno[2,3-b]pyrazolo[3,4-d]pyridin-3-one

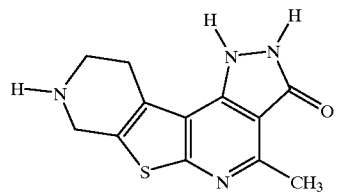

2,3,7,8,9,10-Hexahydro-4-methyl-1H-pyrido[4',3':4,5]thieno[2,3-b]pyrazolo[3,4-d]pyridin-3-one Trifluoroacetate Salt To a suspension of compound of Example 5(e) (0.50 g, 1.39 mmol) in dichloromethane (15 mL) was added trifluoroacetic acid (3 mL) and the resulting clear solution was stirred at room temperature for 1.5 h. The mixture was concentrated under reducer pressure and then diluted with ethyl acetate to yield title compound as a yellowish solid material (0.494 g, 96%). mp 200–203° C. (dec); $^1$H NMR (400 MHz, d$_6$-DMSO) δ4.48 (s, 2 H), 3.55 (t, J=5.6 Hz, 2 H), 3.25 (t, J=5.6 Hz, 2 H), 2.77 (s, 3 H); MS (ESI) m/z 261 [M+H]$^+$.

EXAMPLE 7

An oral dosage form for administering Formula (III) compounds is produced by screening, mixing, and filling into hard gelatin capsules the ingredients in the proportions shown in Table 1, below.

TABLE I

| Ingredients | Amounts |
| --- | --- |
| 8,8-Ethylenedioxy-2,3,7,8,9,10-hexahydro-4-methyl-1H-[1]benzothieno[2,3-b]pyrazolo[3,4-d]pyridin-3-one | 50 mg |
| magnesium stearate | 5 mg |
| lactose | 75 mg |

EXAMPLE 8

The sucrose, calcium sulfate dihydrate and Formula (III) compound shown in Table II below, are mixed and granulated in the proportions shown with a 10% gelatin solution. The wet granules are screened, dried, mixed with the starch, talc and stearic acid, screened and compressed into a tablet.

TABLE II

| Ingredients | Amounts |
| --- | --- |
| 8,8-Ethylenedioxy-2,3,7,8,9,10-hexahydro-4-methyl-1H-[1]benzothieno[2,3-b]pyrazolo[3,4-d]pyridin-3-one | 100 mg |
| calcium sulfate dihydrate | 150 mg |
| sucrose | 20 mg |
| starch | 10 mg |
| talc | 5 mg |
| stearic acid | 3 mg |

EXAMPLE 9

8,8-Ethylenedioxy-2,3,7,8,9,10-hexahydro-4-methyl-1H-[1]benzothieno[2,3-b]pyrazolo[3,4-d]pyridin-3-one, 75 mg, is dispursed in 25 ml of normal saline to prepare an injectable preparation.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound selected from a group consisting of:
   2,3-Dihydro-4-methyl-1H-[1]benzothieno[2,3-b]pyrazolo[3,4-d]pyridin-3-one and pharmaceutically acceptable salts, hydrates and solvates thereof;
   A pharmaceutically acceptable salt, hydrate or solvate of 2,3,7,8,9,10-Hexahydro-4-methyl-1H-[1]benzothieno[2,3-b]pyrazolo[3,4-d]pyridin-3-one;
   1,4-Dimethyl-8,8-ethylenedioxy-2,3,7,8,9,10-hexahydro-1H-[1]benzothieno[2,3-b]pyrazolo[3,4-d]pyridin-3-one and pharmaceutically acceptable salts, hydrates and solvates thereof;
   A pharmaceutically acceptable salt, hydrate or solvate of 8,8-Ethylenedioxy-2,3,7,8,9,10-hexahydro-4-methyl-1H-[1]benzothieno[2,3-b]pyrazolo[3,4-d]pyridin-3-one;
   8-tert-Butoxycarbonyl-2,3,7,8,9,10-hexahydro-4-methyl-1H-pyrido[4',3':4,5]thieno[2,3-b]pyrazolo[3,4-d]pyridin-3-one and pharmaceutically acceptable salts, hydrates and solvates thereof; and
   2,3,7,8,9,10-Hexahydro-4-methyl-1H-pyrido[4',3':4,5]thieno[2,3-b]pyrazolo[3,4-d]pyridin-3-one and pharmaceutically acceptable salts, hydrates and solvates thereof.

2. A method of enhancing erythropoiesis in a subject which comprises administering to a subject in need of such therapy an effective amount of a compound of Formula (III):

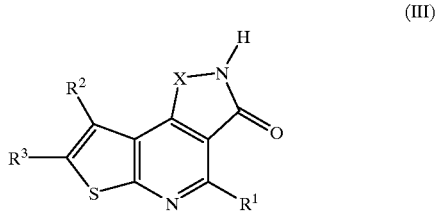

(III)

wherein:

X is O or $NR^5$, where $R^5$ is hydrogen, or is selected from the group consisting of: linear or branched $C_{1-6}$alkyl, —$(CH_2)_nC_{3-7}$cycloalkyl, linear or branched $C_{2-6}$alkenyl, linear and branched $C_{2-6}$alkynyl or —$(CH_2)_n$Ar, all of which are optionally substituted with one or more substituents selected from the group consisting of: —OH, —$OR^6$, —$CONR^6R^7$, —$NR^6R^7$, —$COR^6$, —$CO_2R^6$, —$SO_2NHR^6$, —$NHCOR^6$ and halogen, where n is 0 to 6;

$R^6$ and $R^7$ are:
(i) hydrogen, or independently selected from: linear or branched $C_{1-6}$alkyl, $C_{3-7}$cycloalkyl, linear or branched $C_{2-6}$alkenyl, linear or branched $C_{2-6}$alkynyl and Ar, all of which are optionally substituted with one or more substituents selected from the group consisting of: —OH and halogen, or
(ii) when attached to the same nitrogen atom $R^6$ and $R^7$ together form a ring selected from the group consisting of: piperidyl, morpholynyl, piperazinyl and pyrrolidyl;

$R^1$ is hydrogen, or is selected from the group consisting of: linear or branched $C_{1-6}$alkyl, —$(CH_2)_nC_{3-7}$cycloalkyl, linear or branched $C_{2-6}$alkenyl, linear or branched $C_{2-6}$alkynyl and —$(CH_2)_n$Ar, all of which are optionally substituted with one or more substituents selected from the group consisting of: —OH, —$OR^6$, —$CONR^6R^7$, —$NR^6R^7$, —$COR^6$, —$CO_2R^6$, —$SO_2NHR^6$, —$NHCOR^6$ and halogen, where n, $R^6$ and $R^7$ have the same meaning as above;

$R^2$ and $R^3$ are joined together to form a non-aromatic saturated or unsaturated $C_{5-7}$cycloalkyl, optionally containing one nitrogen heteroatom, and optionally substituted with one or more substituents selected from the group consisting of: ethylenedioxy, linear or branched $C_{1-6}$alkyl, $C_{3-7}$cycloalkyl, phenyl, —OH, —$OR^6$, —$CONR^6R^7$, —$COR^6$, —$CO_2R^6$, —$SO_2NHR^6$, —$NHCOR^6$ and halogen, or $R^2$ and $R^3$ are joined together to form an aromatic ring which is phenyl optionally substituted with one or more substituents selected from the group consisting of: halogen, —OH, linear or branched $C_{1-6}$alkyl, —$(CH_2)_nC_{3-7}$cycloalkyl, linear or branched $C_{2-6}$alkenyl, —$(CH_2)_n$Ph, —O—$C_{1-6}$alkyl, —$CONR^6R^7$, —$NR^6R^7$, —$COR^6$, —$CO_2R^6$, —$SO_2NHR^6$, —$NHCOR^6$ and halogen;

where n, $R^6$ and $R^7$ have the same meaning as above;

or a pharmaceutically acceptable salt, hydrate or solvate thereof.

3. The method of claim 2 in which:

X is $NO^5$;

where $R^5$ is hydrogen, or selected from: linear or branched $C_{1-6}$alkyl, $C_{3-7}$cycloalkyl and phenyl; and $R^1$ is hydrogen, or selected from: linear or branched $C_{1-6}$alkyl, $C_{3-7}$cycloalkyl and phenyl; and $R^2$ and $R^3$ are (i) hydrogen, or independently selected from: linear or branched $C_{1-6}$alkyl, $C_{3-7}$cycloalkyl and phenyl, (ii) $R^2$ and $R^3$ are joined together to form a non aromatic saturated or unsaturated $C_{5-7}$cycloalkyl, optionally containing one nitrogen heteroatom, and optionally substituted with one or more substituents selected from the group consisting of: ethylenedioxy, linear or branched $C_{1-6}$alkyl, $C_{3-7}$cycloalkyl, phenyl, —OH, —$OR^6$, —$CONR^6R^7$, —$COR^6$, —$SO_2R^6$, —$CO_2NHR^6$, —$NHCOR^6$ and halogen, or (iii) $R^2$ and $R^3$ are joined together to form a phenyl ring, optionally substituted with one or more substituents selected from the group consisting of: halogen, —OH, linear or branched $C_{1-6}$alkyl, $C_{3-7}$cycloalkyl and phenyl;

except 2,3,7,8,9,10-Hexahydro-4-methyl-1H-[1]benzothieno[2,3-b]pyrazolo[3,4-d]pyridin-3-one and 8,8-Ethylenedioxy-2,3,7,8,9,10-hexahydro-4-methyl-1H-[1]benzothieno[2,3-b]pyrazolo[3,4-d]pyridin-3-one.

4. The method of claim 2 wherein the compound is selected from a group consisting of:

2,3,7,8,9,10-Hexahydro-4-methyl-1H-[1]benzothieno[2,3-b]pyrazolo[3,4-d]pyridin-3-one and pharmaceutically acceptable salts, hydrates and solvents thereof;

2,3-Dihydro-4-methyl-1H-[1]benzothieno[2,3-b]pyrazolo[3,4-d]pyridin-3-one and pharmaceutically acceptable salts, hydrates and solvates thereof;

8,8-Ethylenedioxy-2,3,7,8,9,10-hexahydro-4-methyl-1H-[1]benzothieno[2,3-b]pyrazolo[3,4-d]pyridin-3-one and pharmaceutically acceptable salts, hydrates and solvates thereof;

1,4-Dimethyl-8,8-ethylenedioxy-2,3,7,8,9,10-hexahydro-1H-[1]benzothieno[2,3-b]pyrazolo[3,4-d]pyridin-3-one and pharmaceutically acceptable salts, hydrates and solvates thereof;

8-tert-Butoxycarbonyl-2,3,7,8,9,10-hexahydro-4-methyl-1H-pyrido[4',3':4,5]thieno[2,3-b]pyrazolo[3,4-d]pyridin-3-one and pharmaceutically acceptable salts, hydrates and solvates thereof; and 2,3,7,8,9,10-Hexahydro-4-methyl-1H-pyrido[4',3':4,5]thieno[2,3-b]pyrazolo[3,4-d]pyridin-3-one and pharmaceutically acceptable salts, hydrates and solvates thereof.

5. A pharmaceutical composition comprising a pharmaceutical carrier and a compound of Formula (III)

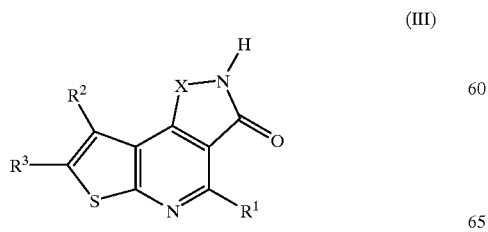

(III)

wherein:

X is O or $NR^5$;

where $R^5$ is hydrogen, or is selected from the group consisting of: linear or branched $C_{1-6}$alkyl, —$(CH_2)_n$$C_{3-7}$cycloalkyl, linear or branched $C_{2-6}$alkenyl, linear and branched $C_{2-6}$alkynyl or —$(CH_2)_n$Ar, all of which are optionally substituted with one or more substituents selected from the group consisting of: —OH, —$OR^6$, —$CONR^6R^7$, —$NR^6R^7$, —$COR^6$, —$CO_2R^6$, —$SO_2NHR^6$, —$NHCOR^6$ and halogen, where n is 0 to 6;

$R^6$ and $R^7$ are:

(i) hydrogen, or independently selected from the group consisting of: linear or branched $C_{1-6}$alkyl, $C_{3-7}$cycloalkyl, linear or branched $C_{2-6}$alkenyl, linear or branched $C_{2-6}$alkynyl and Ar, all of which are optionally substituted with one or more substituents selected from the group consisting of —OH and halogen, or (ii) when attached to the same nitrogen atom $R^6$ and $R^7$ can join together to form a ring selected from the group consisting of: piperidyl, morpholynyl, piperazinyl and pyrrolidyl;

$R^1$ is hydrogen, or is selected from the group consisting of: linear or branched $C_{1-6}$alkyl, —$(CH_2)_n$$C_{3-7}$cycloalkyl, linear or branched $C_{2-6}$alkenyl, linear or branched $C_{2-6}$alkynyl and —$(CH_2)_n$Ar, all of which are optionally substituted with one or more substituents selected from the group consisting of: —OH, —$OR^6$, —$CONR^6R^7$, —$NR^6R^7$, —$COR^6$, —$CO_2R^6$, —$SO_2NHR^6$, —$NHCOR^6$ and halogen, where n, $R^6$ and $R^7$ have the same meaning as above;

$R^2$ and $R^3$ are joined together to form a non-aromatic saturated or unsaturated $C_{5-7}$cycloalkyl, optionally containing one nitrogen heteroatom, and optionally substituted with one or more substituents selected from the group consisting of: ethylenedioxy, linear of branched $C_{1-6}$alkyl, $C_{3-7}$cycloalkyl, phenyl, —OH, —$OR^6$, —$CONR^6R^7$, —$COR^6$, —$CO_2R^6$, —$SO_2NHR^6$, —$NHCOR^6$ and halogen, or $R^2$ and $R^3$ are joined together to form an aromatic ring which is phenyl optionally substituted with one or more substituents selected from the group consisting of: halogen, —OH, linear or branched $C_{1-6}$alkyl, —$(CH_2)_n$$C_{3-7}$cycloalkyl, linear or branched $C_{2-6}$alkenyl, —$(CH_2)_n$Ph, —O—$C_{1-6}$alkyl, —$CONR^6R^7$, —$NR^6R^7$, —$COR^6$, —$CO_2R^6$, —$SO_2NHR^6$, —$NHCOR^6$ and halogen;

where n, $R^6$ and $R^7$ have the same meaning as above;

or a pharmaceutically acceptable salt, hydrate or solvate thereof.

6. A composition of claim 5 wherein the compound is selected from a group consisting of:

2,3,7,8,9,10-Hexahydro-4-methyl-1H-[1]benzothieno[2,3-b]pyrazolo[3,4-d]pyridin-3-one and pharmaceutically acceptable salts, hydrates and solvates thereof;

2,3-Dihydro-4-methyl-1H-[1]benzothieno[2,3-b]pyrazolo[3,4-d]pyridin-3-one and pharmaceutically acceptable salts, hydrates and solvates thereof;

8,8-Ethylenedioxy-2,3,7,8,9,10-hexahydro-4-methyl-1H-[1]benzothieno[2,3-b]pyrazolo[3,4-d]pyridin-3-one and pharmaceutically acceptable salts, hydrates and solvates thereof;

1,4-Dimethyl-8,8-ethylenedioxy-2,3,7,8,9,10-hexahydro-1H-[1]benzothieno[2,3-b]pyrazolo[3,4-d]pyridin-3- one and pharmaceutically acceptable salts, hydrates and solvates thereof;

8-tert-Butoxycarbonyl-2,3,7,8,9,10-hexahydro-4-methyl-1H-pyrido[4',3':4,5]thieno[2,3-b]pyrazolo[3,4-d]pyridin-3-one and pharmaceutically acceptable salts, hydrates and solvates thereof; and 2,3,7,8,9,10-Hexahydro-4-methyl-1H-pyrido[4',3':4,5]thieno[2,3-b]pyrazolo[3,4-d]pyridin-3-one and pharmaceutically acceptable salts, hydrates and solvates thereof.

7. A process for preparing a pharmaceutical composition which process comprises bringing a compound of the formula (III) into association with a pharmaceutically acceptable carrier or diluent wherein Formula (III) is:

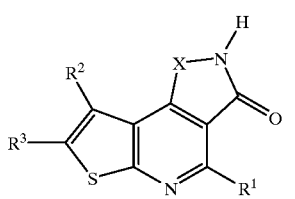

(III)

wherein:

X is O or $NR^5$, where $R^5$ is hydrogen, or is selected from the group consisting of: linear or branched $C_{1-6}$alkyl, $—(CH_2)_nC_{3-7}$cycloalkyl, linear or branched $C_{2-6}$alkenyl, linear and branched $C_{2-6}$alkynyl or $—(CH_2)_n$Ar, all of which are optionally substituted with one or more substituents selected from the group consisting of: —OH, —$OR^6$, —$CONR^6R^7$, —$NR^6R^7$, —$COR^6$, —$CO_2R^6$, —$SO_2NHR^6$, —$NHCOR^6$ and halogen, where n is 0 to 6;

$R^6$ and $R^7$ are:

(i) hydrogen, or independently selected from the group consisting of: linear or branched $C_{1-6}$alkyl, $C_{3-7}$cycloalkyl, linear or branched $C_{2-6}$alkenyl, linear or branched $C_{2-6}$alkynyl and Ar, all of which are optionally substituted with one or more substituents selected from the group consisting of —OH and halogen, or (ii) when attached to the same nitrogen atom $R^6$ and $R^7$ can join together to form a ring selected from the group consisting of: piperidyl, morpholynyl, piperazinyl and pyrrolidyl;

$R^1$ is hydrogen, or is selected from the group consisting of: linear or branched $C_{1-6}$alkyl, $—(CH_2)_nC_{3-7}$cycloalkyl, linear or branched $C_{2-6}$alkenyl, linear or branched $C_{2-6}$alkynyl and $—(CH_2)_n$Ar, all of which are optionally substituted with one or more substituents selected from the group consisting of: —OH, —$OR^6$, —$CONR^6R^7$, —$NR^6R^7$, —$COR^6$, —$CO_2R^6$, —$SO_2NHR^6$, —$NHCOR^6$ and halogen, where n, $R^6$ and $R^7$ have the same meaning as above;

$R^2$ and $R^3$ are joined together to form a non-aromatic saturated or unsaturated $C_{5-7}$cycloalkyl, optionally containing one nitrogen heteroatom, and optionally substituted with one or more substituents selected from the group consisting of: ethylenedioxy, linear or branched $C_{1-6}$alkyl, $C_{3-7}$cycloalkyl, phenyl, —OH, —$OR^6$, —$CONR^6R^7$, —$COR^6$, —$CO_2R^6$, —$SO_2NHR^6$, —$NHCOR^6$ and halogen, or $R^2$ and $R^3$ are joined together to form an aromatic ring which is phenyl optionally substituted with one or more substituents selected from the group consisting of: halogen, —OH, linear or branched $C_{1-6}$alkyl, $—(CH_2)_nC_{3-7}$cycloalkyl, linear or branched $C_{2-6}$alkenyl, $—(CH_2)_n$Ph, —O—$C_{1-6}$alkyl, —$CONR^6R^7$, —$NR^6R^7$, —$COR^6$, —$CO_2R^6$, —$SO_2NHR^6$, —$NHCOR^6$ and halogen;

where n, $R^6$ and $R^7$ have the same meaning as above;

or a pharmaceutically acceptable salt, hydrate or solvate thereof.

\* \* \* \* \*